United States Patent [19]
Chauvette et al.

[11] Patent Number: 5,843,061
[45] Date of Patent: Dec. 1, 1998

[54] FLEXIBLE ABSORBENT SHEET

[75] Inventors: Gaetan Chauvette, Lonevevil; Patricia Ramacieri, Montreal, both of Canada

[73] Assignee: Johnson & Johnson Consumer Products, Inc., Skillman, N.J.

[21] Appl. No.: 723,326

[22] Filed: Sep. 30, 1996

Related U.S. Application Data

[60] Continuation of Ser. No. 484,445, Jun. 7, 1995, which is a division of Ser. No. 732,852, Jul. 19, 1991.

[51] Int. Cl.⁶ .................................................. A61F 13/15
[52] U.S. Cl. ........................... 604/375; 604/374; 604/367
[58] Field of Search ........................... 604/358, 367–368, 604/374–375

[56] References Cited

U.S. PATENT DOCUMENTS

| | | | |
|---|---|---|---|
| 4,432,833 | 2/1984 | Breese | 604/375 |
| 4,605,402 | 8/1986 | Iskra | 604/368 |
| 4,610,678 | 9/1986 | Weisman et al. | 604/368 |

*Primary Examiner*—Robert A. Clarke
*Attorney, Agent, or Firm*—James P. Barr

[57] ABSTRACT

A highly absorbent, flexible and resilient sheet comprising a non-defiberized cellulosic pulp board containing effective amounts of debonding agent and cross-linked cellulosic fibers, well-suited for use as an absorbent component of a disposable, absorbent product such as a sanitary napkin, a diaper, an incontinence pad, an adult brief, a wound dressing and the like. The invention also extends to a method for manufacturing the fluid-absorbent sheet, to a disposable absorbent product utilizing the fluid-absorbent sheet and to a method for enhancing the resilience, fluid-absorbency and flexibility of a non-defiberized cellulosic pulp board.

8 Claims, 3 Drawing Sheets

FLEXIBLE ABSORBENT SHEET

This is a continuation of application Ser. No. 08/484,445, filed Jun. 7, 1995, which is a division of application Ser. No. 07/732,852, filed Jul. 19, 1991, which is hereby incorporated by reference.

FIELD OF THE INVENTION

The invention relates to the art of manufacturing structures for absorbing body exudate. More specifically, the invention relates to a highly absorbent, flexible and resilient, non-defiberized cellulosic pulp material providing a soft, fluid-absorbent component, well-suited for use in disposable absorbent products such as sanitary napkins, diapers, incontinence pads, adult briefs, wound dressings and the like. The invention also extends to a method for manufacturing the fluid-absorbent cellulosic pulp material, to a disposable absorbent product utilizing the fluid-absorbent cellulosic material and to a method for enhancing the resilience, fluid-absorbency and flexibility of non-defiberized cellulosic pulp material.

BACKGROUND OF THE INVENTION

Many disposable absorbent articles use cellulosic pulp fluff material as the absorbent core. Such cores are generally soft, flexible and absorbent but tend to be bulky and thick and have poor wicking properties. In addition, cellulosic pulp fluff cores have poor structural stability, prone to collapsing when wet.

An absorbent structure that has poor wicking properties may increase the likelihood of failure of the absorbent product to hold and contain body fluids. Body fluids will be localized to a certain area of a poorly wicking absorbent core, causing saturation in such area whereby excess fluid may overflow through an external surface of the absorbent product. This overflow may contact the user's garment and cause stains or contact the user's body and cause wet discomfort or rash. It is therefore desirable to provide an absorbent core for disposable absorbent articles which can wick away body fluids from the point of contact with the absorbent core and spread it through the absorbent core to more efficiently utilize the entire surface area of the absorbent core. The improved wicking properties of such an absorbent core provide the capacity for fluids to travel by capillary action throughout the surface area of the absorbent core and thus permit the use of thinner cores, since more absorbent volume can be made available for absorbing body fluids by such wicking action. Thinner absorbent cores may prove to be more comfortable for the user and less unsightly or obvious when worn under clothes.

Absorbent cores with excellent wicking properties comprising peat moss and wood pulp composite materials are described, for example, in U.S. Pat. Nos. 4,170,515; 4,226,237; 4,215,692; 4,507,112; 4,676,871; and 4,473,440. In accordance with the teaching of these patents, an absorbent structure comprising peat moss as a primary absorbent component is formed as a sheet by air or wet laying of fibers and calendering the sheet to obtain a relatively thin, i.e. from about 0.01 to 0.1 inch (in) thick and relatively dense, i.e. from about 0.2 to 1.0 gram per cubic centimeter (g/cc) structure. Such absorbent peat moss sheets may be processed to increase their flexibility by subjecting the sheets to mechanical tenderizing such as by perf-embossing processes as described in U.S. Pat. No. 4,596,567 or microcorrugating processes as described in U.S. Pat. No. 4,605,402.

The peat moss sheets thus formed have a large proportion of extremely tiny pores and capillaries which give them the ability to absorb and retain an enormous capacity of fluid. The peat moss pores swell as they absorb fluid, however, this swelling does not cause a loss of capacity for further absorbing fluid. Rather, the swelling contributes to the ability of the sheet to retain fluid while generally maintaining the structural integrity of the absorbent structure in use.

The wicking properties of the above-described peat moss sheets provide the ability for the sheets to be highly absorbent and thin. The flexibility of peat moss sheets may be improved by perf-embossing and/or microcorrugating processes as described above.

While peat moss sheets make excellent absorbent and wicking cores for disposable absorbent articles, they have limitations. Peat moss sheets may not be readily available particularly in areas which lack the critical raw material, i.e. peat moss or sphagnum moss of desirable age, structure and moisture content. Peat moss sheets also are relatively dark in color and may not be aesthetically acceptable for use in all absorbent products.

Having regard to the foregoing, it is desirable to provide a thin, absorbent and wicking core for disposable absorbent articles which may be substituted for peat moss sheets or cellulosic pulp fluff sheets.

Attempts to utilize other cellulosic pulp materials such as Kraft wood pulp boards as absorbent cores have not been successful because they tend not to have as much absorbent capacity as peat moss composite sheets but more importantly Kraft wood pulp boards cannot be sufficiently softened for their intended use. While the flexibility and other characteristics of such Kraft wood pulp boards may be improved by perf-embossing and/or microcorrugating techniques, such products still do not provide a desirable combination of absorption capacity and fluid penetration, wicking rates and most importantly a sufficient degree of flexibility for optimal use in disposable absorbent products, including packaging materials, tampons and particularly sanitary napkins.

It is, therefore, an object of the present invention to provide a fluid-absorbent cellulosic pulp sheet which does not utilize peat moss in its structure but has sufficient absorption capacity as well as a relatively short fluid acceptance time, and possesses good flexibility and resiliency for use in disposable absorbent articles. Optimal flexibility of such products requires that the product be comfortably soft and flexible to the wearer but stiff and strong enough to withstand bunching and breakage when subjected to mechanical stress in a dry and a wet state.

Another object of the invention is to provide a method for manufacturing such fluid-absorbent cellulosic pulp sheet.

Another object of the invention is to provide a disposable absorbent product which uses such cellulosic pulp sheet as an absorbent component.

Yet, another object of the invention is a method for enhancing the flexibility, resiliency and fluid-absorbency characteristics of non-defiberized cellulosic pulp material.

SUMMARY OF THE INVENTION

Traditionally, cellulosic pulp fluff has been manufactured by grinding a high density cellulosic pulp board in a mill which mechanically ruptures the physical interfiber bonds to produce a fibrous network, the so-called "fluff", with a very high void volume. An important economic factor in any process to convert cellulosic pulp boards into fluff material is the energy cost for operating the grinding mill. It is generally accepted that regardless of the kind of equipment used for the conversion, the cost of energy is a significant factor in the overall conversion expenditure.

To reduce the energy consumption of a grinding mill, it is common practise to incorporate in the cellulosic pulp board a debonding agent which acts to reduce the forces uniting the cellulosic fibers, by providing a steric hindrance. As a result, less energy is required to defiberize the cellulosic pulp board. The most popular debonding agents which are commercially available from various sources are based on quaternary amonium compounds. Canadian patent number 1,152,710 granted to Kimberly-Clark Corporation on Aug. 30, 1983, describes a debonder of this class. Debonding agents are also described and disclosed in U.S. Pat. No. 4,482,429 at col. 4, lines 8–36; U.S. Pat. Nos. 3,972,855; 4,144,122; and 4,432,833. The entire disclosure of these references are hereby incorporated by reference. It has also been suggested to treat a cellulosic pulp board with debonding agent and then perf-emboss the debonded pulp board to reduce its stiffness to acceptable levels for use as an absorbent core in a disposable absorbent product. The combination of debonding and perf-embossing increases the absorption and flexibility of the cellulosic pulp board.

As a substitute to chemical debonding agents, it has been suggested to introduce in the cellulosic pulp board cross-linked cellulosic fibers providing a high-bulk, resilient structure acting to maintain a certain spacing between the fibers of the cellulosic pulp board, to achieve a reduction in the cohesiveness of the fibrous network. As an example, the U.S. Pat. No. 4,853,086 granted to Weyerhaueser Company on Aug. 1, 1989 describes a method for manufacturing such cross-linked cellulosic fibers. In essence, the method consists of spraying a wet or partially dried web of cellulosic fibers with an aqueous solution of a glycol and dialdehyde.

The present inventors have made the unexpected discovery that by incorporating a debonding agent and cross-linked cellulosic fibers to a board of cellulosic pulp, a synergy effect develops, vastly improving the resiliency, flexibility and fluid-absorbency (for the purpose of this specification, "fluid-absorbency" shall solely mean the ability of a body to take-up fluid, regardless of how fluid-retentive the body is. For example, the transfer layer of a compound absorbent structure, provided to meter fluid to the reservoir layer, will be described as fluid-absorbent although it has a relatively poor fluid retentivity) of the board, providing a soft, highly absorbent sheet that may be used in a non-defiberized form as an absorbent component for disposable absorbent products such as sanitary napkins, diapers, adult briefs, incontinence pads, wound dressing and the like. A particularly significant advantage of this absorbent structure resides in that no defiberization is required, which considerably reduces the manufacturing cost of the absorbent structure.

The debonding agent (for the purpose of this specification "debonding agent" should be construed to include any agency acting chemically on the cellulose fibers to reduce the incidence of hydrogen bonding between the fibers by steric hindrance action) cooperates with the cross-linked cellulosic fibers to provide the essential ingredients necessary to relax the fibrous network of the cellulosic material. More specifically, the debonding agent weakens the interfiber bonds, while the cross-linked cellulosic fibers provide, by virtue of their inherent resiliency, an expansion force pushing the fibers away from one another. The resulting fibrous network has a void volume which is high enough to provide an excellent fluid-absorption capacity and a high fluid-acceptance rate, while remaining below the level beyond which the structural integrity of the fluid-absorbent sheet is compromised in use. The increase in the inter-fiber distances also provides the fibrous network with the ability to flex under low effort and to return to its original configuration upon the cessation of the deformation effort. These characteristics provide increased comfort potential allowing the fluid-absorbent, non-defiberized cellulosic sheet to be used as an absorbent component in disposable absorbent products for use next to the body.

Interestingly, the fluid-absorbent cellulosic sheet is particularly stable in a wet condition, exhibiting only a limited collapse upon fluid take-up. This phenomenon is attributable to the ability of the cross-linked cellulosic fibers to maintain the fibers of the fluid-adsorbent cellulosic sheet in a spaced apart relationship in the presence of a fluid medium.

In a preferred embodiment, the fluid-absorbent cellulosic sheet comprises cross-linked, fibrous cellulosic material in the range from about 1 to about 99 percent based on the dry weight of cellulose. The debonding agent is present in the fluid-absorbent cellulosic sheet in the range from about 0.05 to about 10 percent based on the dry weight of cellulose.

Advantageously, the fluid-absorbent cellulosic sheet is mechanically tenderized by perf-embossing or microcorrugation to increase its flexibility for further enhancing its comfort potential.

The starting material for manufacturing the fluid-adsorbent cellulosic sheet is preferably selected from the group consisting of sulfate, sulfite, debonded, bleached, unbleached, Kraft wood pulp, thermo-mechanical pulp, chemical thermal mechanical pulp, wood pulp bleached by a chlorine process and wood pulp bleached by hydrogen peroxide.

As embodied and broadly described herein, the invention further comprises a method for manufacturing a non-defiberized, fluid-absorbent sheet, comprising the step of incorporating in a cellulosic pulp board effective amounts of cross-linked cellulosic fibers and debonding agent to enhance the resiliency, flexibility and fluid-adsorbency of said cellulosic pulp board.

In a preferred embodiment, the cross-linked cellulosic fibers are added to a slurry of cellulosic pulp which is used for making the cellulosic pulp board. The slurry is then formed into a web and dewatered to obtain the highly resilient and flexible, fluid-absorbent cellulosic sheet. The debonding agent may be added to the slurry or applied to the web in a dried or partially dried condition such as by spraying, soaking or kissing.

As embodied and broadly described herein, the invention also provides a method for increasing the resilience, flexibility and fluid-absorbency of a non-defiberized cellulosic pulp board, comprising the step of incorporating in said cellulosic pulp board effective amounts of debonding agent and cross-linked cellulosic fibers.

As embodied and broadly described herein, the invention also extends to a disposable, laminated, fluid absorbent product such as a sanitary napkin, a diaper, an adult brief, an incontinence pad, a wound dressing and the like, comprising:
  a) a fluid-permeable cover layer;
  b) a fluid-impervious backing layer in a generally parallel and spaced apart relationship with said fluid-permeable cover layer; and
  c) an absorbent component between said layers, said absorbent component comprising a non-defiberized cellulosic pulp board containing effective amounts of debonding agent and cross-linked cellulosic fibers, enhancing the resiliency, flexibility and fluid-absorbency of said pulp board.

The fluid-absorbent cellulosic sheet according to the invention may also be utilized in other absorbent products such as inserts for tampons, or as desiccants for use in packaging materials to keep goods dry during shipping or storage.

DESCRIPTION OF A PREFERRED EMBODIMENT

Figure 1:
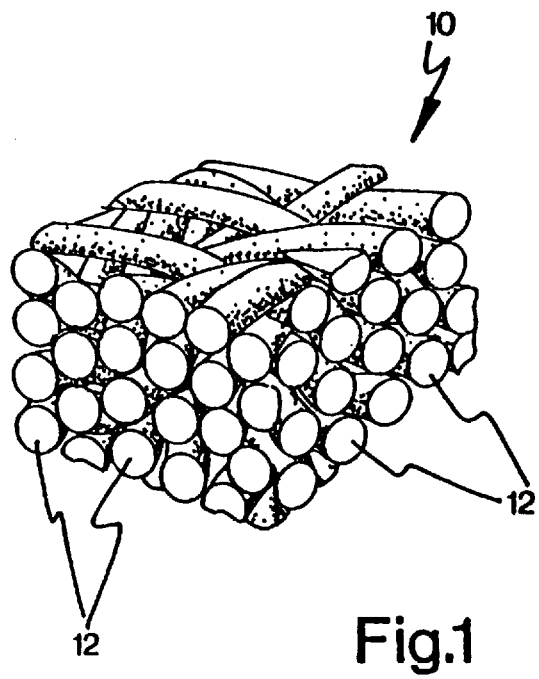
FIG. 1 is an idealized perspective view at the fiber level of a cellulosic pulp board in raw form, i.e. free of agents that hinder the hydrogen bonding between the cellulosic fibers.

FIG. 1 is an idealized, perspective view on a highly enlarged scale of the fibrous network 10 of a cellulosic pulp board in raw form. It should be understood that this representation is solely for illustrative purposes and it does not necessarily conform to the true material structure of the cellulosic pulp board.

The fibrous network 10 is composed of individual cellulosic fibers 12, which are randomly oriented and are united to one another by hydrogen bonding. The fibers 12 form a highly dense and cohesive network with only a limited amount of void volume therebetween. This translates into poor fluid-absorption properties and into a rigid, relatively non-conformable structure, making the cellulosic pulp board unsuitable for use as an absorbent layer in a disposable absorbent product.

In order to reduce the cohesiveness of the fibrous network 10, primarily for facilitating its mechanical defiberization, the prior art teaches to incorporate in the fibrous network 10 cross-linked cellulosic fibers providing a high-bulk, resilient structure which functions to physically space the fibers 12 from one another.

Figure 2:
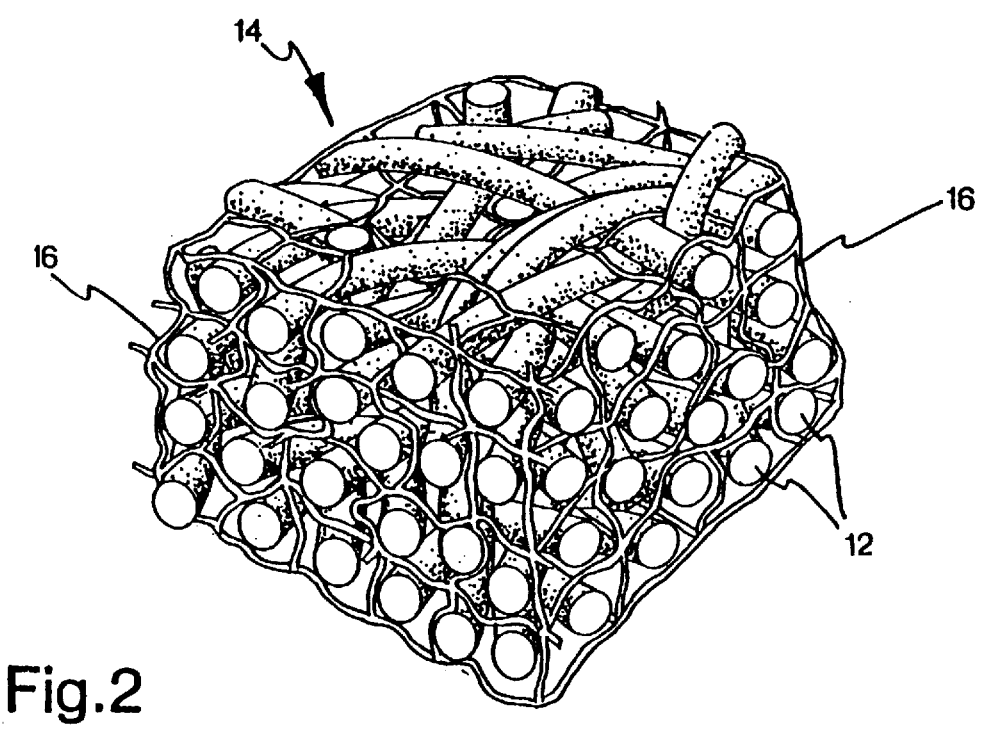
FIG. 2 illustrates the network of the cellulosic pulp board of FIG. 1 in which cross-linked cellulosic fibers have been incorporated.

FIG. 2 illustrates schematically a cellulosic fibrous network 14 containing cross-linked cellulosic fibers 16. The cross-linked fibers 16, forming a space frame-like structure are uniformly interspersed with the fibers 12 and, by virtue of their inherent resiliency, urge the fibers 12 away from one another. However, it is believed that the hydrogen bonding between the fibers 12 remains very strong and greatly overwhelms the resistance to deformation of the cross-linked cellulosic fibers 16. As a result, the space frame-like structure is in a virtually collapsed condition, achieving only a limited reduction in cohesiveness of the fibrous network 14. The reduction in structural integrity of the fibrous network 14 considerably reduces the energy required to mechanically defiberize it, however, it does not sufficiently improve its fluid-absorbency, resiliency and flexibility to allow the fibrous network 14 to be advantageously used as an absorbent component in a disposable absorbent product.

The method for manufacturing the cross-linked cellulosic fibers 16 will not be described herein because this technology is well documented in the patent literature. For example, U.S. Pat. No. 4,853,086 discloses a process for manufacturing the cross-linked cellulosic fibers by spraying a wet or only partially dried cellulosic fibrous web with an aqueous solution of a glycol and dialdehyde. The entire disclosure of this patent reference is hereby incorporated herein by reference.

Figure 3:
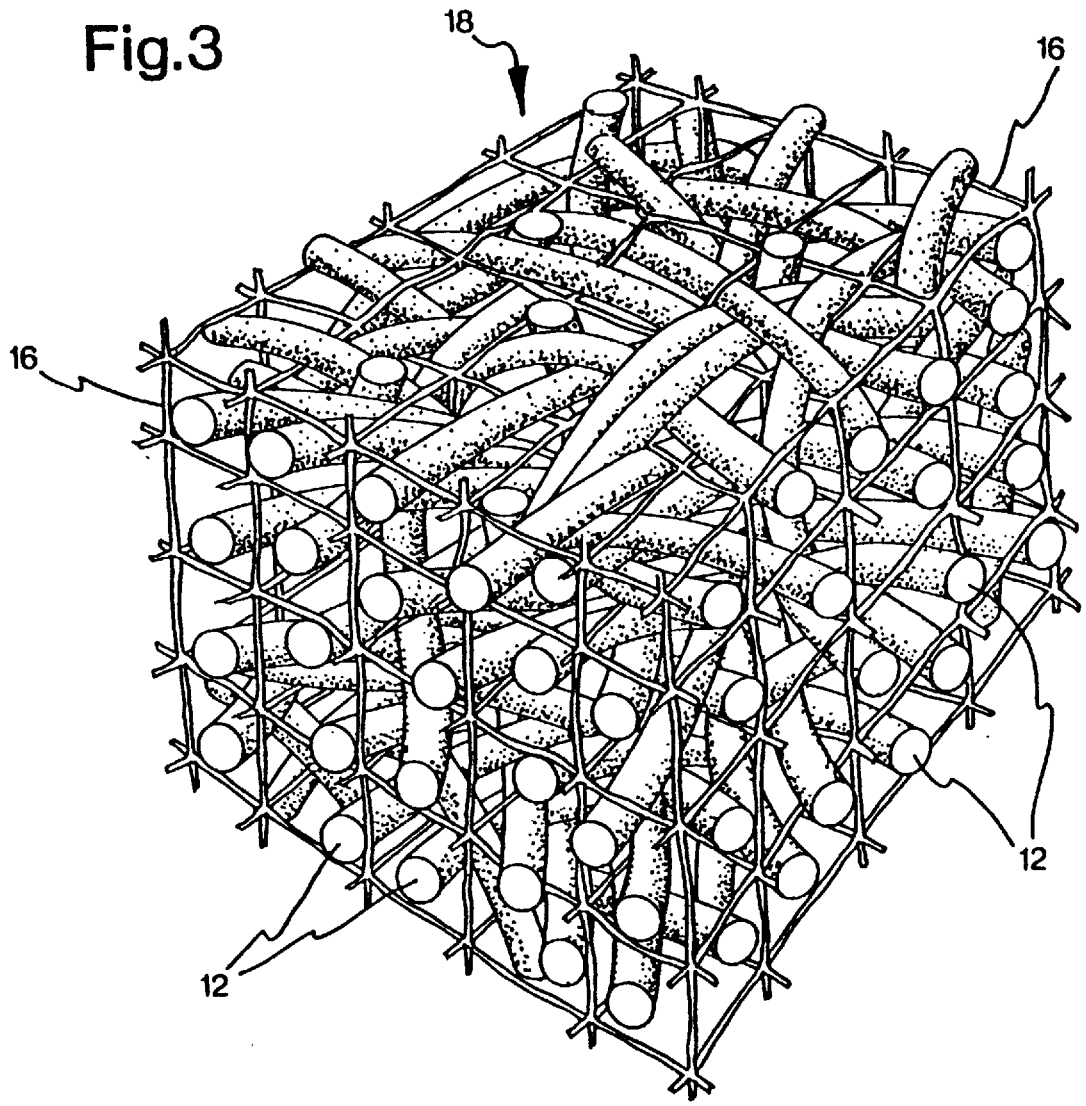
FIG. 3 is an idealized view of the fibrous network shown in FIG. 2 in which a debonding agent has been incorporated.

FIG. 3 illustrates a cellulosic pulp board treated with a debonding agent and containing cross-linked cellulosic fibers 16. It is apparent that the fibrous network 18 is considerably more relaxed than the fibrous network 14, exhibiting comparatively large interfiber distances which translate into a higher void volume and an increased, overall bulk. The significant improvement in bulking by comparison to the fibrous network 14 shown in FIG. 2 is attributable to the debonding agent which inhibits the hydrogen bonding between the fibers, reducing the forces collapsing the space frame-like structure formed by the cross-linked cellulosic fibers 16. As a result, the space frame-like structure expands the entire fibrous network 18 by virtue of its ability of rebound or shape recovery after deformation.

The fibrous network 18 is advantageous for use in a non-defiberized form as an absorbent component for a disposable absorbent product such as a sanitary napkin, a diaper, an incontinence pad, an adult brief, a wound dressing and the like. It offers exceptional fluid absorption properties such as a good capacity and a high fluid-acceptance rate as well as good wicking characteristics. In addition, it has a good comfort potential because it is soft and flexible, providing an absorbent product which is highly conformable to the area of the body to which it is intended to be applied, thus providing good gasketing properties, i.e. the ability to conform to the surface of the body. In addition, the fibrous network 18 is capable to maintain its integrity in the dry and in the wet state. Further, its degree of collapse upon taking-up fluid is relatively small, providing a good structural integrity in the presence of a fluid medium.

The various fluid-absorbency characteristics of the fibrous network 18 may be tailored according to the intended application by varying the density of the fibrous network 18. For example, by decreasing the density of the fibrous network 18, the fluid-acceptance rate increases at the expense of fluid retentivity and capacity. Such a structure would be suitable as a transfer layer in a compound absorbent component for metering fluid to a reservoir layer. Conversely, an increase of density will favour the fluid-absorbency requirements for a reservoir layer. For a single layer absorbent structure, the density is selected to provide the necessary balance between the various fluid-absorbency characteristics.

The fluid-absorbent cellulosic pulp sheet according to the invention is manufactured by incorporating into a slurry of cellulosic pulp material cross-linked cellulosic fibers prepared in accordance with the process generally set forth in U.S. Pat. No. 4,853,086. The percentage of cross-linked cellulosic fibers in the slurry is in the range from about 1 to about 99 percent based on the dry weight of cellulose.

The appropriate debonding agent is also added in the slurry of cellulosic material, in the range from about 0.05 to about 10 percent based on the weight of cellulose. A hydrophilic debonder has been found satisfactory. (By "hydrophilic debonder" is meant a debonding agent that preserves the hydrophilic nature of the cellulosic material). U.S. Pat. No. 4,432,833 discloses various hydrophilic quaternary amine debonders and U.S. Pat. Nos. 3,972,855 and 4,144,122 disclose various debonding agents including the commercially available BEROCELL 584 debonding agent which is a particularly preferred debonding agent for use in the present invention. The disclosure of the various debonding agents in these patents is hereby incorporated herein by reference.

The slurry is formed into a web and dewatered to form the fluid-absorbent cellulosic sheet.

In a variant, the debonding agent may be incorporated into the cellulosic material after the slurry has been formed into a web. For example, the debonding agent may be sprayed on one or on both sides of the web, or the web may be soaked into a solution of debonding agent for a deeper penetration. Also, a kissing technique may be employed, as described in Canadian patent number 596,894 issued on Apr. 26, 1960 to Chicopee Manufacturing Corporation, U.S.A. The entire disclosure of this reference is hereby incorporated herein by reference.

The starting material for making the slurry of cellulosic material is selected from the group consisting of sulfate, sulfite, debonded, bleached, unbleached, Kraft wood pulp, thermo-mechanical pulp, chemical thermal mechanical pulp, wood pulp bleached by a chlorine process and wood pulp bleached by hydrogen peroxyde and mixtures thereof.

In order to further tenderize, soften and improve the flexibility of the fluid-absorbent cellulosic sheet, it may be subjected to mechanical tenderizing by perf-embossing or microcorrugating processes as generally described in the United States patents granted to Personal Products Company, U.S. Pat. Nos. 4,596,567 and 4,559,050, issued on Jun. 24, 1986 and Dec. 17, 1985, respectively (which are hereby incorporated herein by refeence).

Broadly stated, the perf-embossing operation consists of perforating by shearing action, at a multiplicity of points the fluid-absorbent cellulosic sheet to open up its structure by locally disrupting the integrity of the fibrous network 18. Subsequently, the fluid-absorbent cellulosic sheet is embossed transversely and longitudinally by passing the sheet between rolls having intermeshing flutes. The embossing lines created constitute hinges which considerably enhance the flexibility of the sheet.

The microcorrugating operation is similar to the perf-embossing process except that no perforation is performed. The fluid-absorbent cellulosic sheet is solely subjected to a lateral embossing operation to create closely spaced hinge lines.

Figure 4:
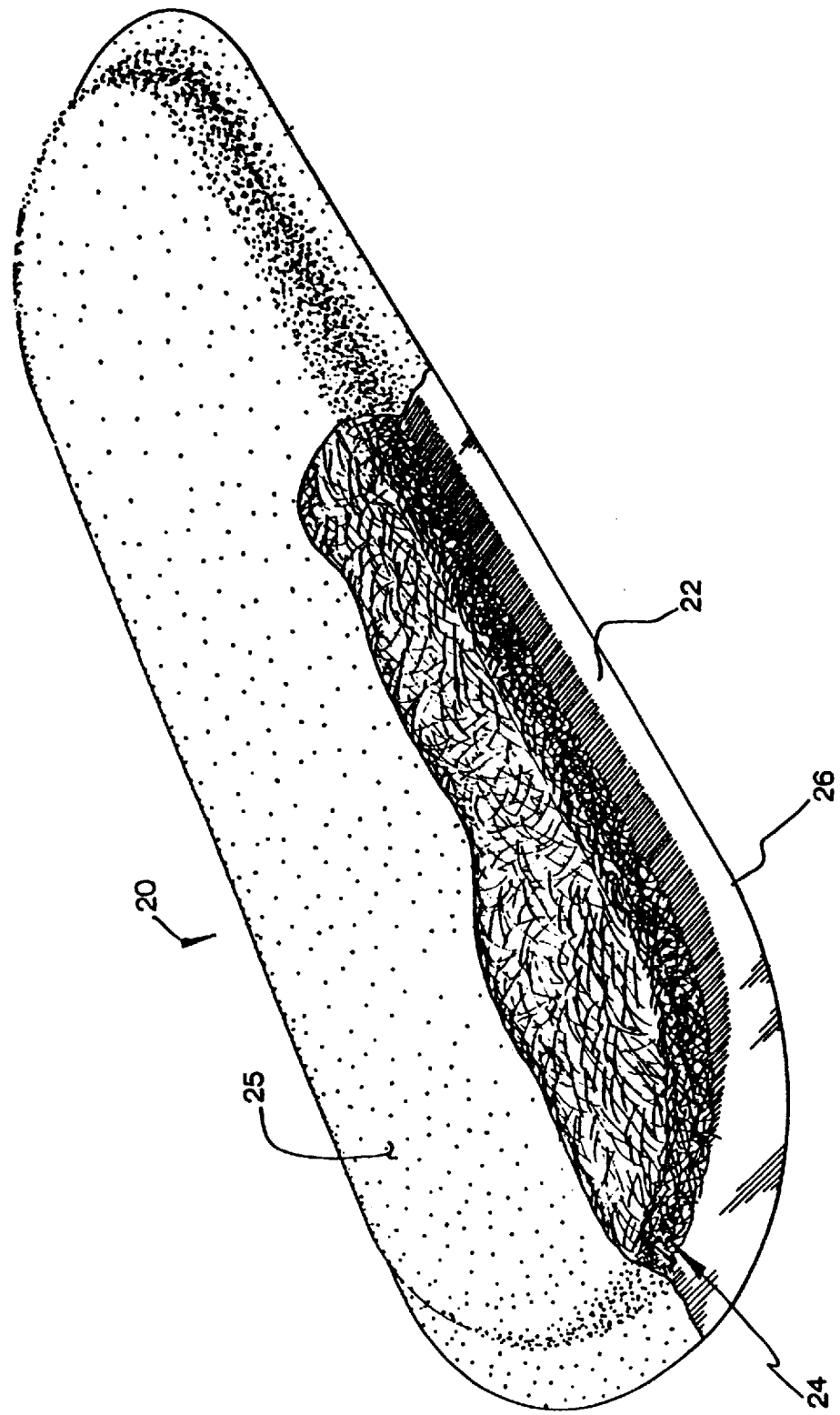
FIG. 4 is a fragmentary, perspective view of a sanitary napkin incorporating the fluid-absorbent cellulosic sheet according to the invention.

FIG. 4 illustrates a sanitary napkin incorporating the fluid-absorbent cellulosic sheet according to the invention. The sanitary napkin, designated comprehensively by the reference numeral 20, comprises an envelope 22 defining an internal space receiving an absorbent component 24. The envelope 22 includes a fluid-permeable cover layer 25 made of non-woven fabric or any other suitable porous web, and a fluid-impervious backing layer 26 made of polyethylene film, for example. The cover and backing layers 25 and 26 are heat-sealed to one another along their marginal portions.

The absorbent component 24 may have a single or a double layer configuration. In the former case, depicted in FIG. 4, the absorbent component 24 is an insert constituted by the fluid-absorbent cellulosic sheet according to the invention. In the latter case (not shown in the drawings), the absorbent component has a top layer, referred to as a transfer layer and a bottom layer, designated as a reservoir layer. The fluid-absorbent cellulosic sheet is particularly suitable for use as a transfer layer due to its high fluid-acceptance rate, coupled in an intimate fluid-communicative relationship with a reservoir layer made of any suitable highly absorbent and retentive material. In a variant, the fluid-absorbent cellulosic sheet may be adapted for reservoir layer duty or use by increasing its density, as previously described.

To attach the sanitary napkin 20 to the wearer's underpants, the fluid-impervious backing layer 26 is provided with adhesive zones covered with a peelable backing (not shown in the drawings).

Sanitary napkins constructed in accordance with the present invention are found to possess a very high fluid-absorption capacity and a comparatively high fluid-acceptance rate which reduces the risk of failure when a large quantity of fluid is suddenly released on the sanitary napkin. In addition, the sanitary napkin is thin, soft and flexible so as to be comfortable to the user and to conform well to the surface of the body to which it is applied to achieve good gasketing effects.

The scope of the present invention is not limited by the description, examples and suggestive uses herein, as modifications can be made without departing from the spirit of the invention. Applications of the product and methods of the present invention for sanitary and other health-care uses can be accomplished by any sanitary protection, incontinence, medical and absorbent methods and techniques that are presently or prospectively known to those skilled in the art. For example, the absorbent products and methods of the invention can be applied to wound dressings or other useful absorbent products. Thus, it is intended that the present application cover the modifications and variations of this invention provided that they come within the scope of the appended claims and their equivalents.

We claim:

1. A disposable, laminated fluid-absorbent product comprising:

a) a fluid-permeable cover layer;

b) a fluid-impervious backing layer in a generally parallel and spaced apart relationship with said fluid permeable cover layer; and c) an absorbent component between said layers, said absorbent component comprising a non-defiberized cellulosic pulp board containing a debonding agent and cross-linked cellulosic fibers said cross-linked cellulosic fibers having been formed by treating noncross-linked cellulosic fibers with a glycol having a formula $HO-(CH_2)_mO)_n-H$ where m is 2 or 3 and n is in the range 1 to 500, and a dialdehyde having a formula $OCH(CHX)_n-CHO$ wherein n is in the range 0 to 4 and X is hydrogen of hydroxyl, and wherein the debonding agent and the cross-linked cellulosic fibers are present in an amount effective to enhance the flexibility and fluid penetration of the absorbent component.

2. A fluid-absorbent product as defined in claim 1, wherein said non-defiberized cellulosic pulp board is mechanically tenderized to enhance its flexibility.

3. A fluid-absorbent product as defined in claim 1, wherein said non-defiberized cellulosic pulp board is mechanically tenderized by a process selected from the group consisting of perf-embossing and microcorrugating.

4. A fluid-absorbent product as defined in claim 1, wherein said non-defiberized cellulosic pulp board comprises cross-linked cellulosic fibers in the range from about 1 to about 99 percent by weight based on the dry weight of cellulose in said pulp board.

5. A fluid-absorbent product as defined in claim 1, wherein said debonding agent is present in said non-defiberized cellulosic pulp board in the range from about 0.05 to about 10 percent based on the dry weight of cellulose in said pulp board.

6. A fluid-absorbent product as defined in claim 1, wherein said debonding agent is hydrophilic.

7. A fluid-absorbent product as defined in claim 1, wherein said non-defiberized cellulosic pulp board includes material selected from the group consisting of sulfate, sulfite, debonded, bleached, unbleached, Kraft wood pulp, thermo-mechanical pulp, chemical thermal mechanical pulp, wood pulp bleached by a chlorine process and wood pulp bleached by hydrogen peroxide and mixtures thereof.

8. A fluid-absorbent product as defined in claim 1, wherein said absorbent component includes a top transfer layer and a bottom reservoir layer, said non-defiberized cellulosic pulp board constituting either one of said transfer and reservoir layers.

* * * * *